（12） United States Patent  
Gibson et al.

(10) Patent No.: US 8,141,417 B2
(45) Date of Patent: Mar. 27, 2012

(54) SYRINGE CONTENT DETECTION USING RF ENERGY

(75) Inventors: Chad M. Gibson, Mason, OH (US); Vernon D. Ortenzi, Burlington, KY (US)

(73) Assignee: Mallinckrodt LLC, Hazelwood, MO (US)

( * ) Notice: Subject to any disclaimer, the term of this patent is extended or adjusted under 35 U.S.C. 154(b) by 518 days.

(21) Appl. No.: 12/439,184

(22) PCT Filed: Aug. 6, 2008

(86) PCT No.: PCT/US2008/072304
§ 371 (c)(1),
(2), (4) Date: Feb. 27, 2009

(87) PCT Pub. No.: WO2009/025996
PCT Pub. Date: Feb. 26, 2009

(65) Prior Publication Data
US 2009/0322545 A1    Dec. 31, 2009

Related U.S. Application Data

(60) Provisional application No. 60/957,539, filed on Aug. 23, 2007.

(51) Int. Cl.
*G01F 13/00* (2006.01)
*G08B 21/00* (2006.01)
*G01R 27/04* (2006.01)
*A61M 5/36* (2006.01)

(52) U.S. Cl. ........................... 73/149; 324/639; 604/151

(58) Field of Classification Search .................. 73/149; 324/639; 604/151
See application file for complete search history.

(56) References Cited

U.S. PATENT DOCUMENTS

| 4,006,736 A | 2/1977 | Kranys et al. |
| 4,107,993 A | 8/1978 | Shuff et al. |
| 5,206,522 A | 4/1993 | Danby et al. |
| 5,602,828 A | 2/1997 | Engdahl et al. |
| 5,662,612 A | 9/1997 | Niehoff |
| 5,681,286 A | 10/1997 | Niehoff |
| 6,004,292 A | 12/1999 | Battiato et al. |

(Continued)

FOREIGN PATENT DOCUMENTS
EP    0 372 700    6/1990
(Continued)

OTHER PUBLICATIONS

Beach et al., "A bubble detector for automatic analgesic drug injectors", Journal of Phys. E: Sci. Instrum., vol. 13, 1980, pp. 1053-1054.

*Primary Examiner* — Daniel Larkin
(74) *Attorney, Agent, or Firm* — Marsh Fischmann & Breyfogle LLP

(57) ABSTRACT

The present invention includes medical fluid injector systems that detect the contents and/or volume of such contents within a syringe of the system. For example, an RF signal from a first antenna of a medical fluid injector may be transmitted through a syringe associated with the medical fluid injector. At least some of the transmitted RF signal may be received by a second antenna of the medical fluid injector. An amount of the RF signal received by the second antenna may be measured to provide information regarding the contents and/or volume of such contents within the syringe.

26 Claims, 3 Drawing Sheets

U.S. PATENT DOCUMENTS

| | | | |
|---|---|---|---|
| 6,780,170 B2 | 8/2004 | Fago et al. | |
| 6,811,517 B1 | 11/2004 | Eschenbach | |
| 7,482,818 B2 * | 1/2009 | Greenwald et al. | 324/639 |
| 7,698,180 B2 * | 4/2010 | Fago et al. | 705/28 |
| 2005/0156607 A1 | 7/2005 | Okamura | |
| 2006/0079842 A1 | 4/2006 | Small et al. | |
| 2006/0079843 A1 * | 4/2006 | Brooks et al. | 604/151 |
| 2007/0000321 A1 | 1/2007 | Boudaoud et al. | |

FOREIGN PATENT DOCUMENTS

| | | |
|---|---|---|
| EP | 1 736 189 | 12/2006 |
| JP | 60-214226 | 10/1985 |
| WO | WO 2006/006643 | 1/2006 |
| WO | WO 2006/108026 | 10/2006 |
| WO | WO 2007/121398 | 10/2007 |

* cited by examiner

SYRINGE CONTENT DETECTION USING RF ENERGY

RELATED APPLICATIONS

This application claims priority to U.S. provisional application Ser. No. 60/957,539 filed on 23 Aug. 2007 and entitled "Syringe Content Detection Using RF Energy".

FIELD OF THE INVENTION

The present invention relates to systems for detecting medical fluid and/or air (e.g., air bubbles) in a syringe of a medical fluid injector system.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

In many medical environments, a medical fluid is injected into a patient during diagnosis or treatment. One example is the injection of contrast media into a patient to improve CT, Angiographic, Magnetic Resonance, or Ultrasound imaging, using a catheter inserted into a patient's blood vessel.

One of the dangers involved when using a contrast media in the aforementioned procedures is the risk that air from an empty or partially filled syringe may be accidentally injected into the patient. An errant air injection is a risk because a beating heart relies upon the non-compressibility of blood to vacate the blood from ventricle to ventricle by compression. Unlike blood however, air is compressible. The presence of a compressible gas in a heart ventricle can create a situation similar to a "vapor lock", which effectively stops the heart from pumping blood to the body due to a loss of pressure. This situation (commonly referred to as an air embolism) is created when a large amount of air (e.g., 50-60 cc's) is injected rapidly (e.g., as with an injector used in an angiographic scan) and travels to the heart.

Procedures employed for the operation of contrast media injectors in CT, Angiographic, MRI, and Cardiology departments include a human operator checking that syringes are correctly loaded and filled. However, even in facilities that have safety procedures established, human errors can still result. These errors may lead to situations where an air-filled syringe that was thought to be full of contrast media is errantly injected into a patient, and the patient experiences an air embolism. For instance, medical staff using an angiographic injector may mistakenly assume that an empty, used or unused syringe (which was left in the injector at the end of a previous session) is full and may errantly inject the air from the empty syringe into a patient, thus potentially causing an air embolism.

To further compound the potential for error, contrast media used in medical imaging procedures is frequently colorless, and at least some of such procedures tend to be performed under relatively low light levels to facilitate reading of the resulting images. Both of these factors may tend to increase the chance of error. As such, some users may find an injector system that allows for syringe fill volume detection quite desirable.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

A first aspect of the invention is directed to a syringe mount for a medical fluid injector. This syringe mount includes a source of RF energy, as well as first and second antennae. The first antenna of the syringe mount is utilized to transmit RF energy (e.g., at a given frequency) from the source of RF energy. The second antenna of the syringe mount is utilized to receive at least some of the RF energy transmitted from the first antenna. These first and second antennae are generally located proximate to a syringe (that may or may not include an RFID tag) when the syringe is mounted on the syringe mount, such that at least part of the RF energy that is transmitted from the first antenna travels through the syringe prior to being received by the second antenna.

In some embodiments, the syringe mount may include a third antenna that is configured to receive RF energy transmitted from the first antenna. This third antenna may be located proximate to the syringe when the syringe is mounted on the syringe mount. The third antenna may be positioned such that at least part of the RF energy transmitted from the first antenna travels through the syringe prior to being received by the third antenna.

In some embodiments, the second antenna may be coupled to an RF receiver. This RF receiver may be configured to measure change (e.g., a decrease) in RF energy received by the second antenna from the first antenna.

In some embodiments, the frequency of RF energy transmitted though the first antenna of the syringe mount may be fixed at a predetermined frequency and/or magnitude. In contrast, other embodiments may allow for frequency and/or magnitude of the RF energy to be adjustable.

Still referring to the first aspect of the invention, the antennae may exhibit any appropriate design and/or configuration. For instance, the antennae may be any of a dipole, loop, monopole, or other appropriate RF antenna structures.

A second aspect of the invention is directed to a method of operation for a medical fluid injector. In this method, an RF signal is transmitted from a first antenna of the medical fluid injector through a syringe associated with the medical fluid injector. This RF signal that is transmitted may be any appropriate wavelength. For instance in some embodiments, the RF signal exhibits a wavelength smaller than a diameter of the syringe. At least some of the RF signal is received by a second antenna of the medical fluid injector, and the amount of the RF signal that is received by the second antenna is measured (e.g., by measurement of power).

A variety of different actions may be initiated based, at least in part, on the measured amount of the RF signal received by the second antenna. For example, in some embodiments, the medical fluid injector may be disabled (e.g., if the measured RF signal received is indicative of air being present in the syringe). In some embodiments, initiation of an injection protocol may be enabled (e.g., if the measured RF signal received is indicative of little or no air being present in the syringe). For example, if the measured RF signal received is indicative of little or no air being present in the syringe, a controller of the injector may cause the injector to be enabled so an operator can start an injection procedure (e.g., by pressing a button, touch screen, trigger, etc.). In some embodiments, a programmed injection protocol may automatically (e.g., without user involvement) be initiated (e.g., if the measured RF signal received is indicative of little or no air being present in the syringe).

The amount of the RF signal received and measured may be utilized to determine if medical fluid is present within the syringe. In some embodiments, the amount of the RF signal received and measured may be utilized to determine an approximate volume of medical fluid in the syringe. The amount of the RF signal received by the second antenna may be compared to an amount of the RF signal transmitted from the first antenna and/or one or more predetermined RF signal values. This comparison may be utilized in determining the content (e.g., air and/or medical fluid) of and/or volume of medical fluid in the syringe.

In some embodiments, the medical fluid injector may automatically become disabled if the determined approximate volume of medical fluid in the syringe is less than that required to perform a programmed injection protocol. In some embodiments, the medical fluid injector may automatically provide an audible warning, a visible warning, or a combination thereof if the determined approximate volume of medical fluid in the syringe is less than that required to perform a programmed injection protocol.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein.

DETAILED DESCRIPTION OF THE FIGURES

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Injector systems disclosed herein may be characterized as having beneficial functionality in the form of an integrated radiofrequency transponder that allows for syringe fill volume detection. Specifically, systems disclosed herein integrate two or more radiofrequency antennas and their associated electronics into an injector. These antennas may be attached to electronics that enable appropriate radiofrequency transmission and receipt. The antennas may be designed as dipoles, loop antennas, or any other antenna capable of emitting RF energy.

With regard to exemplary transponders of the invention, one or more antennas may radiate RF energy, which may be received by one or more different antennas. The RF energy may be adjustable in one or both frequency and magnitude. The RF energy may be fixed in one or both frequency and magnitude. Further, the RF energy may be turned on and off.

The antennas may be located in any appropriate location on the injector. For instance, in some embodiments, the antennas are located in proximity to a syringe holding mechanism of the injector. When the syringe is placed in the holding mechanism, fluid in the will attenuate (reduce) the signal flowing from the transmitting antenna to the receiving antenna.

The receiving antenna measures a lower power RF signal than that emitted by the transmitting antenna. By measuring the magnitude of the power decrease, disclosed injector systems are able to determine whether a syringe is filled with a contrast fluid or filled with air. Further, some injector systems disclosed herein may have an RF transponder system that enables the injector to determine how much fluid (e.g., contrast media) is confined in the syringe.

Figure 1:
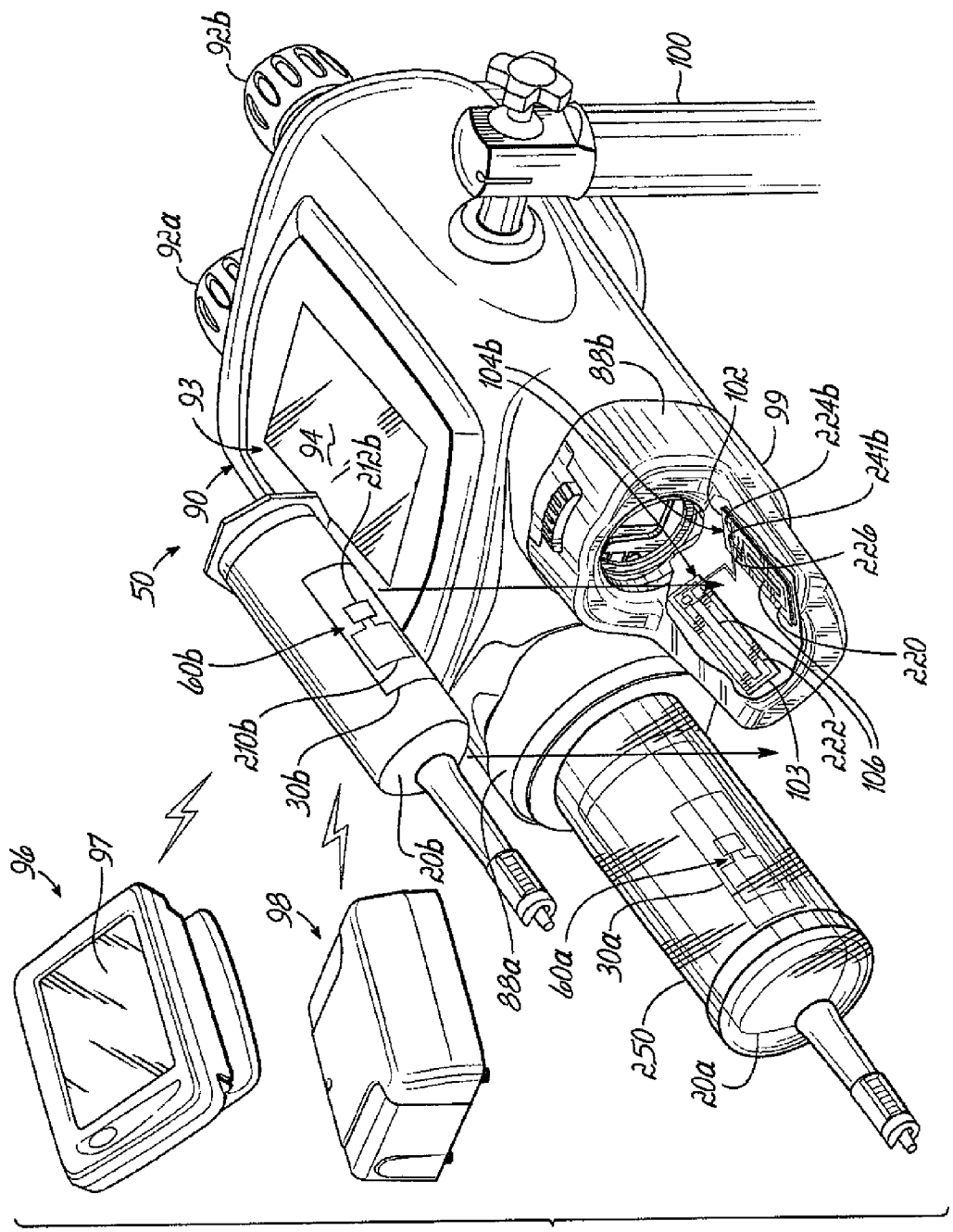
FIG. 1 is a perspective view of an exemplary embodiment illustrating a syringe positioned above a faceplate of a contrast media power injector having multiple, nonparallel antenna loops for a read/write device.

Referring to FIG. 1, an injector system 50 includes various functional components, such as a powerhead 90, a console 96 and power pack 98. Syringes 20*a* and 20*b* are mounted to the injector powerhead 90 in faceplates 88*a* and 88*b* of the powerhead 90, and the various injector controls are used to fill the syringes with medical fluid (e.g., contrast media), which is then injected into a patient via operator or pre-programmed control of the injector system 50.

The powerhead 90 of the injector system 50 includes hand-operated knobs 92*a* and 92*b* for use in manually controlling the movement of the internal drive motors engaged to syringes 20*a* and 20*b*, and a touch screen display 94 for indicating to the operator the current status and operating parameters of the injector. The console 96 also includes a touch screen display 97 that may be used by the operator to remotely control operation of the injector powerhead 90, and may also be used to specify and store programs for automatic injection by the injector, which can later be automatically executed by the injector upon initiation by the operator.

Powerhead 90 and console 96 connect through cabling (not shown) to the power pack 98. Power pack 98 includes a power supply for the injector, interface circuitry for communicating between the console 96 and powerhead 90, and further circuitry permitting connection of the injector system to remote units such as remote consoles, remote hand or foot control switches, and/or other original equipment manufacturer (OEM) remote control connections allowing, for example, operation of injector system to be synchronized with operation of an imaging system.

Powerhead 90 is mounted to a stand (not shown) which includes a support arm 100 for supporting powerhead 90 for easy positioning of powerhead 90 in the vicinity of the examination subject. Console 96 and power pack 98 may be placed on a table or mounted on an electronics rack in an examination room. Other installations are also contemplated. For example, powerhead 90 may be supported by a ceiling, floor or wall mounted support arm.

The one or more syringes 20a, 20b are loaded into respectively one or both of the mounts or faceplates 88a, 88b that are attachable on powerhead 90. Exemplary details of an injector like that shown in FIG. 1 are shown and described in U.S. patent application Ser. No. 10/964,003. In the illustrated application, the injector receives multiple syringes: a user-filled syringe having a volume of about 200 ml may be mounted in a pressure jacket 250 of faceplate 88a, and another syringe (e.g., a pre-filled syringe) 20b having a volume in excess of about 90 ml or more may be mounted in faceplate 88b. When the syringes are mounted, the plunger drives of the injector are operable to move plungers within the respective syringes 20a, 20b in a known manner. Exemplary operations of a powerhead 90 and injector control 93 are shown and described in U.S. Pat. No. 7,507,221. Additional exemplary operations are described in U.S. Pat. Nos. 5,662, 612, 5,681,286 and 6,780,170.

As noted, the injector powerhead 90 includes a touch screen 94, providing a user interface for displaying current status and setting operating parameters of the injector system 50, integrated into the surface of the housing of powerhead 90. Powerhead 90 may be mounted to a wheeled stand (partially shown at 100), which permits positioning of the powerhead 90 in the vicinity of the examination subject. The console 96 may be used by an operator to enter programs and control the operation of the injector 50 from a remote location in a known manner.

It will be appreciated that elements of the injector control 93 may be incorporated into the powerhead 90 or may be incorporated in other elements of the injector such as the power supply 98 or console 96, or may be distributed among these elements. The powerhead touch screen 94 and console 96 touch screen 97 display graphic representations of the respective syringes mounted in the powerhead 90, the operation of the powerhead, and the like.

It will be noted that syringes 20a and 20b have RFID tags 60a and 60b thereon, integrated into labels 30a and 30b thereon. The RFID tags 60a, 60b include a chip 212b and antenna loop 210b, which interact with radiofrequency fields generated by antennae in the faceplate, as discussed below. The data contained on the RFID tag 60a or 60b may be displayed on the touch screens 94 and 97, allowing the operator to view and check the data at any time before as well as allowing data to be written into a history file on the RFID tag after an injection has been performed, which may be later accessed. Furthermore, the RFID tag 60a or 60b is capable of storing various data values; information regarding the use of the syringe and or its manufacture may be displayed on the touch screens 94 and 97. Further details on the use of RFID tags and the information that may be stored thereon is provided in PCT Application PCT/US2006/012620, filed Apr., 4, 2006, entitled SYSTEMS AND METHODS FOR MANAGING INFORMATION RELATING TO MEDICAL FLUIDS AND CONTAINERS THEREFOR.

Faceplate 88b has an outward extending cradle 99 that supports a first printed circuit ("PC") board 102 and a second PC board 103, mounted in faceplate 88b so as to be nonparallel. As illustrated in FIG. 1, the PC boards 102, 103 form sides of a V-shape, and thus, there is an angle of less than 180 degrees therebetween. PC board 102 supports a first conductive loop operating as an antenna 220, and its associated tuning circuit 226, and PC board 103 supports a second conductive loop operating as an antenna 222 and its associated tuning circuit. The first and second antenna loops 220, 222 and respective tuning circuits are connected to an RAN RF driver circuit 224b through a switching circuit 241b to collectively form an electromagnetic RAW device 104b. In some embodiments, the RAN RF driver circuit 224b and switching circuit 241b may be mounted on a separate PC board 102b (shown in phantom), which is located beneath, and electrically connected to, the PC board 102. In other embodiments, the RAW RF driver circuit 224b and/or the switching circuit 241b may be mounted in the power head 90 in association with the injector control 93. It will be appreciated, as noted in the above-referenced patent applications, that antennae 220 and 222 may be used in read-write operations in conjunction with an RFID tag 30b on syringe 20b. However, in addition, or in the alternative, antennae 220 and 222 may be used in accordance with principles of the present invention to evaluate the fluid content within syringe, as explored in substantially greater detail in connection with the following discussion of FIGS. 3A, 3B and 4.

Circuit boards 102 and 103 incorporate heaters 106 in the form of resistive traces on PC boards 102 and 104. The heaters 106 are electrically connected to the injector control via a cable or connector and are operable by the injector control circuitry to heat syringe 20b.

Figure 2:
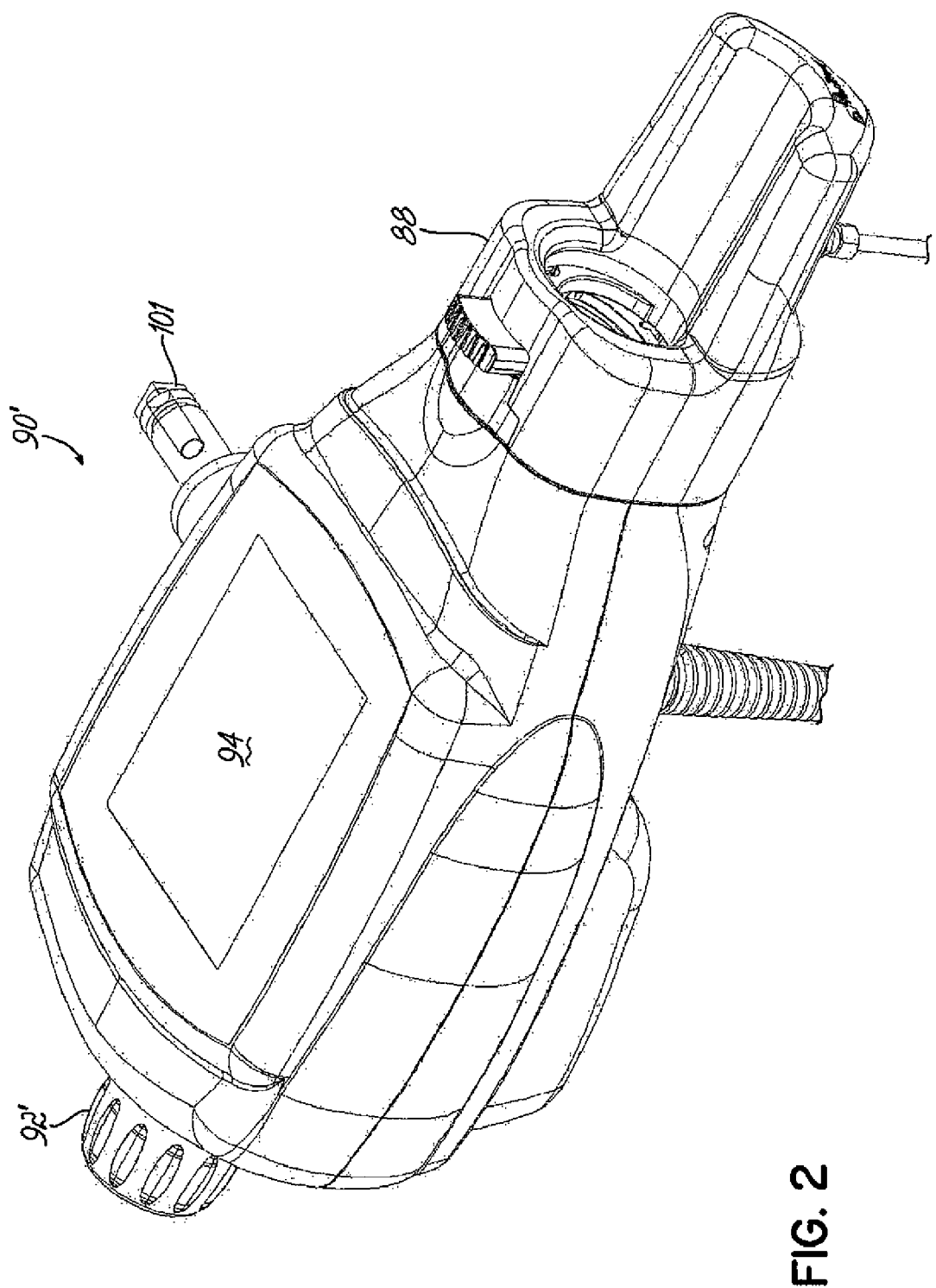
FIG. 2 is a perspective view of an exemplary embodiment illustrating a single head contrast media power injector having multiple, nonparallel antenna loops for a read/write device.

Although the powerhead 90 discussed above and shown in FIG. 1 is a dual head injector, embodiments of the present invention contemplate single head injectors as well. A suitable single-head powerhead 90' is shown in FIG. 2. This single-head powerhead 90' incorporates only a single faceplate 88, which may be of similar construction to the faceplate 88b shown and discussed above with reference to FIG. 1. A single knob 92' is coupled to the drive mechanism within powerhead 90' to allow manual operation of that drive system. Powerhead 90' further incorporates a touch screen 94 for providing a user interface in the manner of the touch screen 94 shown in FIG. 1, although that user interface, by virtue of the single-head powerhead 90', includes controls for a single syringe powerhead. Powerhead 90' includes a mounting 101 for coupling to a mounting arm as is the case in dual-syringe powerhead 90 of FIG. 1, such as the arm 100 (see FIG. 1) of a stand.

While injectors illustrated in the figures include removable faceplates (e.g., 88) as the syringe mounts of those injectors, the present invention is applicable to medical fluid injectors in which the syringe mount(s) is(are) substantially integral with (e.g., not removable or not easily removable from) a housing of the powerhead.

Figure 3A:
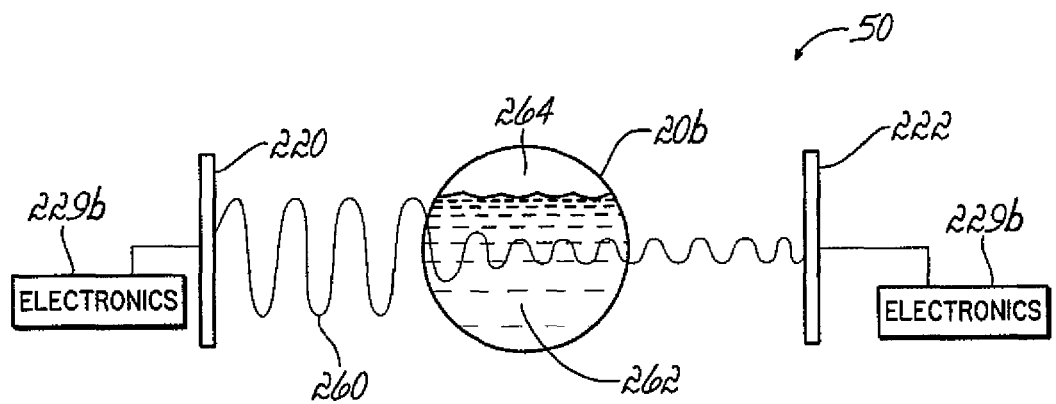
FIG. 3A is a diagrammatic cut away view of an exemplary embodiment illustrating a liquid filled syringe placed between two antenna loops.

FIG. 3A is a schematic representation of an embodiment for explaining the detection of the fill volume in a syringe 20b using one transmitting conductor behaving as antenna 220 and one receiving conductor behaving as antenna 222. The positioning of syringe 20b, transmitting antenna 220, receiving antenna 222, RF energy 260, medical fluid (e.g., contrast media, saline, or a combination thereof) 262, and air 264 are schematically depicted in the system 50.

Figure 3B:
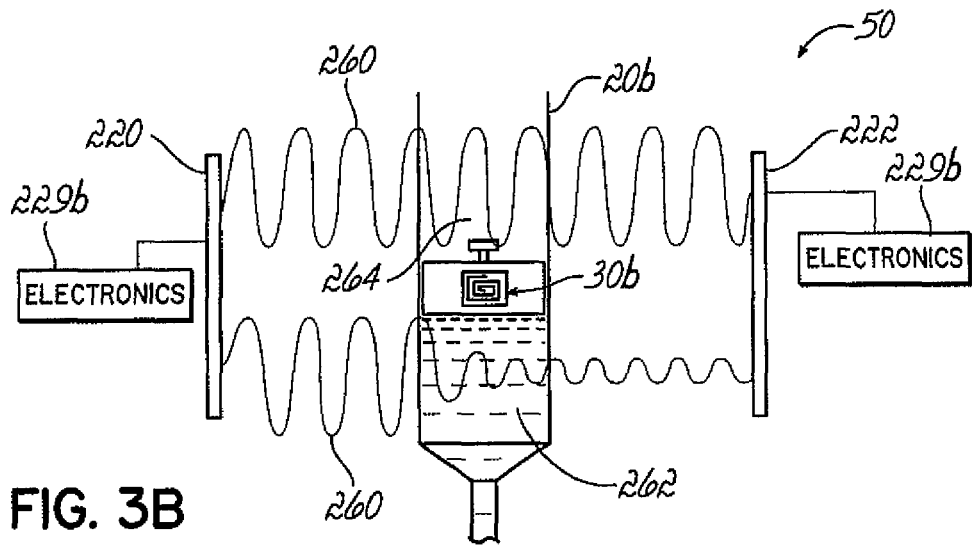
FIG. 3B is a diagrammatic top view of an exemplary embodiment illustrating a liquid filled syringe placed between two antenna loops.

FIG. 3B is a schematic top view explaining the detection of the fill volume in the syringe 20b using one transmitting conductor behaving as the antenna 220, and one receiving conductor behaving as the antenna 222.

In the embodiments schematically illustrated in FIGS. 3A and 3B, the conductors which behave as the transmitting antenna 220 and the receiving antenna 222 are attached to electronics 229b that enable transmission and detection of RF energy 260 through the syringe 20b. Block 229b represents all of the electronics that drive the transmitting antenna and receiving antenna. Examples of such electronics include a tuning circuit 226, an RF driver circuit 224b, and a switching circuit 241b. The syringe 20b may have an RFID tag 30b affixed thereto. It will be appreciated that antennas 220, 222 may be designed as loop antennas as shown in FIG. 1, or may alternatively be dipoles, or any other appropriate structures capable of emitting and receiving RF energy 260.

The magnitude of RF energy 260 received by the antenna 222 from the transmitting antenna 220 will vary depending on whether the syringe is filled with medical fluid 262, a mixture of medical fluid and air 264, or full of air 264 only. By analyzing the amount of RF energy 260 received by the antenna 222 relative to the amount of RF energy 260 transmitted by the antenna 220, the system 50 is able to determine whether the syringe 20b is filled with medical fluid 262, a mixture of medical fluid 262 and air 264, or air 264. If air 264 is detected, typically from reduced attenuation of signal received by antenna 222, then a signal can be triggered to prevent an injection from proceeding.

Additionally, the system may be able to determine an approximate volume of medical fluid 262 present by calculating the amount of RF energy 260 received by the antenna 222. If the volume of medical fluid 262 present falls outside of a predetermined parameter, a signal can be triggered to prevent an injection from proceeding.

Figure 4:
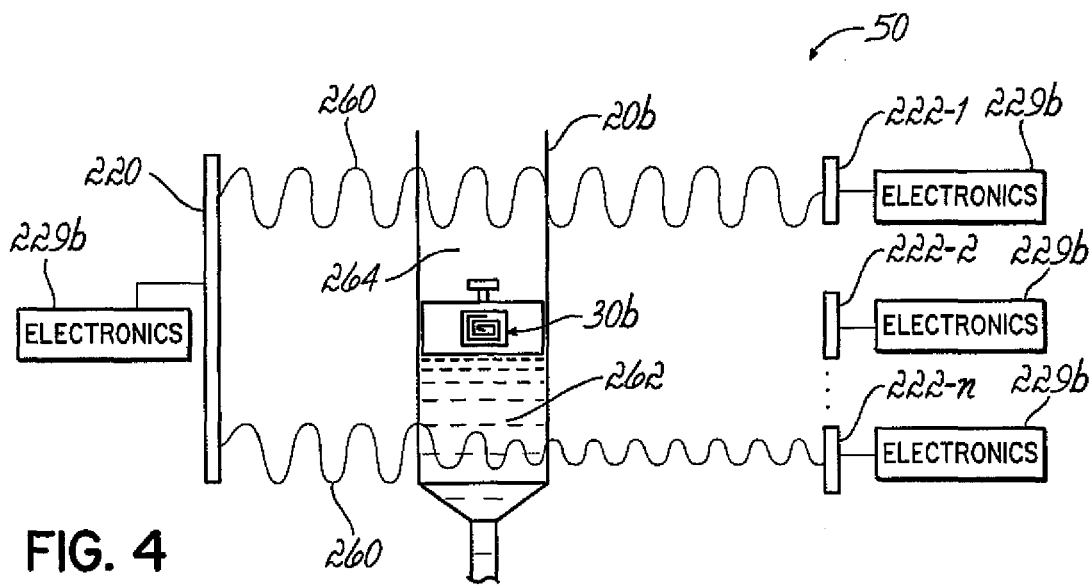
FIG. 4 is a diagrammatic cut away view of an exemplary embodiment illustrating a liquid filled syringe placed between a plurality of antenna loops.

FIG. 4 is a schematic top view of an embodiment for detecting the fill volume in a syringe using multiple receiving conductors behaving as antennas 222-1 and 222-2 and one transmitting conductor behaving as antenna 220. A syringe 20b, transmitting antenna 220, receiving antennae 222-1 and 222-2, RF energy 260, medical fluid 262, and air 264 are exemplified in the system 50. Other embodiments may include any appropriate number of transmitting and receiving conductors.

In the embodiment illustrated in FIG. 4, the conductors behaving as a transmitting antenna 220 and receiving antennae 222-1 and 222-1 are attached to electronics 229b that enable transmission and detection of RF energy 260 through the syringe 20b. An RFID tag 30b is affixed to the syringe 20b, and both medical fluid 262 and air 264 may be found in the syringe 20b. The antennae are disposed along a length of the syringe 20b. Again, these antennae 220, 222-1, 222-2 may be designed as dipoles, loop antennas, or any other appropriate structures capable of emitting and receiving RF energy 260.

Similar to FIG. 3, the magnitude of RF energy 260 received by antennae 222-1 and 222-2 from the transmitting antenna 220 will vary depending on the contents of the syringe 20b. However, unlike the previous embodiment, the multiple receiving antennae 222-1 and 222-2 of the FIG. 4 embodiment will provide enhanced resolution of the amount of contrast in the syringe and/or the location of the plunger based upon the relative attenuation detected at antenna 222-1 and 222-2, and may provide improved error rejection (such as errors that may be caused by noise, attenuation from injector parts such as the ram, and other sources of variation in the RF attenuation between antenna 220 and antennae 222-1 and 222-2).

While the various principles of the invention have been illustrated by way of describing various exemplary embodiments, and while such embodiments have been described in considerable detail, there is no intention to restrict, or in any way limit, the scope of the appended claims to such detail. Additional advantages and modifications will readily appear to those skilled in the art.

For example, in the described embodiments, the syringes used with the injector system included RFID tags 30, however, principles of the present invention may be used on syringes and injectors that do not include RFID functions. Further, in the exemplary embodiments shown herein, the antenna systems use two and three antenna loops; however, in alternative embodiments, any number of antenna loops may be used. The antenna loops may be configured in any shape, and be in the same plane or in different planes, directly opposition one another or in an angled configuration as is shown in FIG. 1. Further, the antenna loops may or may not be overlapping. It may, however, be preferable that the antenna loops be individually tuned to resonate at a specific frequency used by the RFID protocol or other frequencies licensed for use in low power RF applications. Further, in the described embodiment, a switching circuit 241b is located on the same PC board 102 as an RF driver circuit 224b; however, in alternative embodiments, a switching circuit may be located on the second PC board 103, be split between the two PC boards 102, 103 or located elsewhere, for example, within the powerhead.

In addition, in the described embodiments, the antenna systems are applied to an injector; however, in alternative embodiments, the antenna systems for detecting fluid within a syringe may be applied to any devices that support a medical fluid container. Such devices include but are not limited to a warmer oven or warming box, a container filling station, a pig or other nuclear medicine container, a dose calibration station, a handheld powered medical fluid dispenser, a syringe disposal station, or other device.

The systems of the described embodiments relate to containers of medical fluids. Examples described in detail relate to contrast media and syringes containing that media. In alternative embodiments, the container may be a bag filled with a medical fluid. The bag may have a label 30 with a data tag 60 as previously described herein, for example, an RFID tag, or may not be so equipped.

There are many known structures for mounting a syringe to a power injector, and the faceplates shown and described herein are only two such structures. Other mounting structures may not permit removal from the power head. The inventions claimed herein can be applied to power heads having any type of structure for mounting a syringe thereto. In the shown and described embodiment, a heater 106 is mounted on the PC boards 102, 103; however, in alternative embodiments, the heater 106 may not be used and therefore, deleted from PC boards 102, 103.

When introducing elements of the present invention or various embodiments thereof, the articles "a", "an", "the", and "said" are intended to mean that there are one or more of the elements. The terms "comprising", "including", and "having" are intended to be inclusive and mean that there may be additional elements other than the listed elements. Moreover, the use of "top" and "bottom", "front" and "rear", "above" and "below" and variations of these and other terms of orientation is made for convenience, but does not require any particular orientation of the components.

As various changes could be made in the above-described aspects and exemplary embodiments without departing from the scope of the invention, it is intended that all matter contained in the above description shall be interpreted as illustrative and not in a limiting sense.

What is claimed is:

1. A syringe assembly comprising:
 a syringe mount; and
 a syringe mounted on the syringe mount, the syringe mount comprising:
  a source of RF energy;
  a first antenna to transmit RF energy from the source, wherein the first antenna is located proximate to the syringe on the syringe mount; and a second antenna to receive RF energy transmitted from the first antenna, wherein the second antenna is located proximate to the syringe on the syringe mount, and wherein the second antenna is positioned such that at least part of the RF energy that is transmitted from the first antenna travels through the syringe prior to receipt by the second antenna.

2. The syringe assembly of claim 1, further comprising a third antenna configured to receive RF energy from the first antenna, wherein the third antenna is located proximate to the syringe on the syringe mount, and wherein the third antenna is positioned such that at least part of the RF energy that is transmitted from the first antenna travels through the syringe prior to receipt by the third antenna.

3. The syringe assembly of claim 1, further comprising an RF receiver, wherein the second antenna is coupled to the RF receiver.

4. The syringe assembly of claim 3, wherein the RF receiver is configured to measure change in RF energy received by the second antenna from the first antenna.

5. The syringe assembly of claim 1, wherein the first and second antennae are dipole antennas.

6. The syringe assembly of claim 1, wherein the first and second antennae are loop antennas.

7. The syringe assembly of claim 1, wherein the RF energy from the source is adjustable in frequency.

8. The syringe assembly of claim 1, wherein the RF energy from the source is adjustable in magnitude.

9. The syringe assembly of claim 1, wherein the RF energy from the source is transmitted at a fixed, predetermined frequency.

10. The syringe assembly of claim 1, wherein the RF energy from the source is transmitted at a fixed, predetermined magnitude.

11. The syringe assembly of claim 1, wherein the syringe comprises an RFID tag.

12. A medical injector system comprising the syringe assembly of claim 1, wherein the medical injector system is configured to compare an amount of the RF energy transmitted from the first antenna with an amount of the RF energy received by the second antenna to determine content within the syringe.

13. A medical injector system comprising the syringe assembly of claim 1, wherein the medical injector system is configured to compare an amount of the RF energy transmitted from the first antenna with an amount of the RF energy received by the second antenna to determine if medical fluid is present within the syringe.

14. A medical injector system comprising the syringe assembly of claim 1, wherein the medical injector system is configured to compare an amount of the RF energy transmitted from the first antenna with an amount of the RF energy received by the second antenna to determine an approximate amount of medical fluid in the syringe.

15. A medical injector system comprising the syringe assembly of claim 1, wherein the medical injector system is configured to compare an amount of the RF energy transmitted from the first antenna with an amount of the RF energy received by the second antenna to determine whether the syringe is filled with: a) medical fluid; b) a mixture of medical fluid and air; or c) air.

16. A method of operation for a medical fluid injector, the method comprising:
transmitting an RF signal from a first antenna of a medical fluid injector through a syringe associated with the medical fluid injector;
receiving at least some of the RF signal via a second antenna of the medical fluid injector; and
measuring an amount of the RF signal received by the second antenna.

17. The method of claim 16, further comprising:
disabling the medical fluid injector based, at least in part, on the measuring.

18. The method of claim 16, further comprising:
enabling initiation of an injection protocol based, at least in part, on the measuring.

19. The method of clam 16, further comprising:
automatically initiating a programmed injection protocol based, at least in part, on the measuring.

20. The method of claim 16, further comprising:
comparing the amount of the RF signal received by the second antenna to an amount of the RF signal transmitted from the first antenna.

21. The method of claim 16, further comprising:
determining if medical fluid is present within the syringe, wherein the determining is based, at least in part, on the measuring.

22. The method of claim 16, further comprising:
determining an approximate volume of medical fluid in the syringe, wherein the determining is based, at least in part, on the measuring.

23. The method of claim 22, further comprising:
disabling the medical fluid injector if the determined approximate volume is less than that required to perform a programmed injection protocol.

24. The method of claim 22, further comprising:
providing an audible warning, a visible warning, or a combination thereof if the determined approximate volume is less than that required to perform a programmed injection protocol.

25. The method of claim 16, wherein the RF signal has a wavelength smaller than a diameter of the syringe.

26. The method of claim 16, further comprising:
determining whether the syringe is filled with: a) medical fluid; b) a mixture of medical fluid and air; or c) air, all from the measuring.

* * * * *